US010155715B2

(12) United States Patent
Dhar et al.

(10) Patent No.: US 10,155,715 B2
(45) Date of Patent: Dec. 18, 2018

(54) PURIFIED CROCETIN COMPOUND AND METHOD FOR TREATING, INHIBITING, AND/OR PROPHYLAXIS OF CANCER, SUCH AS PANCREATIC CANCER

(75) Inventors: Animesh Dhar, Fairway, KS (US); William G. Gutheil, Kansas City, MO (US)

(73) Assignees: The United States of America as represented by the Department of Veterans Affairs, Washington, DC (US); University of Kansas, Lawrence, KS (US); University of Missouri, Columbia, MO (US)

( * ) Notice: Subject to any disclaimer, the term of this patent is extended or adjusted under 35 U.S.C. 154(b) by 0 days.

(21) Appl. No.: 13/883,061

(22) PCT Filed: Oct. 7, 2011

(86) PCT No.: PCT/US2011/001735
§ 371 (c)(1),
(2), (4) Date: May 2, 2013

(87) PCT Pub. No.: WO2012/060854
PCT Pub. Date: May 10, 2012

(65) Prior Publication Data
US 2013/0231300 A1    Sep. 5, 2013

Related U.S. Application Data

(60) Provisional application No. 61/344,879, filed on Nov. 2, 2010.

(51) Int. Cl.
| | |
|---|---|
| *C07C 57/13* | (2006.01) |
| *A61K 45/06* | (2006.01) |
| *A61K 31/202* | (2006.01) |
| *A61K 31/225* | (2006.01) |
| *A61K 31/513* | (2006.01) |
| *A61K 31/7068* | (2006.01) |

(52) U.S. Cl.
CPC ............ *C07C 57/13* (2013.01); *A61K 31/202* (2013.01); *A61K 31/225* (2013.01); *A61K 31/513* (2013.01); *A61K 31/7068* (2013.01); *A61K 45/06* (2013.01)

(58) Field of Classification Search
CPC ........ C07C 57/13; A61K 31/202; A61K 45/06
USPC .............................. 514/49, 274, 574; 562/595
See application file for complete search history.

(56) References Cited

U.S. PATENT DOCUMENTS

| | | | |
|---|---|---|---|
| 2006/0194973 A1 | 8/2006 | Gainer et al. | |
| 2006/0276372 A1 | 12/2006 | Lockwood et al. | |
| 2010/0210572 A1 | 8/2010 | Eidenberger | |
| 2014/0221491 A1* | 8/2014 | Dhar et al. ............... | 514/574 |

OTHER PUBLICATIONS

Glossary of medical education terms, Institute of International Medical Education. http://www.iime.org/glossary.htm Accessed in Mar. 2013.*
Bold et al. Gemcitabine-Induced Programmed Cell Death (Apoptosis) of Human Pancreatic Carcinoma is Determined by Bcl-2 Content. Ann Surg Oncol 6:279-285, 1999.*
Ozeki et al. A Reversed-Phase Thin-Layer Chromatography/Scanning Densitometric Method for the Analysis of Gardenia Yellow. J. Liq. Chrom. & Rel. Technol., 24(18), 2849-2860 (2001) (Year: 2001).*
PCT International Search Report and the Written Opinion dated Mar. 2, 2012, in International Appl. No. PCT/US2011/001735, filed Oct. 7, 2011. (9 pp.).
Dhar et al. Crocetin inhibits pancreatic cell proliferation and tumor progression in xenograft mouse model., Mol Cancer Ther 2009;8:315-323. Published Online First Feb. 10, 2009.
Jemal, A., Siegel, R., Ward, E., Hao, Y., Xu, J. and Thun, M.J. Cancer Statistics, 2009. CA Cancer J. Clin 59, 225-249, 2009.
Chua, Y.J. and Zalcberg, J.R. Pancreatic Cancer—is the wall crumbling? Annals of Oncology 19, 1224-1230, 2008.
Nair, S.C., Panikkar, B. and Panikkar, K.R. Antitumor activity of saffron (Crocus sativus). Cancer Lett. 1991:57: 109-114.
Abdullaev, F.I. Cancer chemopreventive and tumoricidal proporties of saffron (Crocus sativus L.) Exp. Biol. Med. 2002:227: 20-25.
Abdullaev, F.I. and Espinosa-Aguirre, J.J. Biomedical properties of Saffron and its potential use in cancer therapy and chemoprevention trials (2004) Cancer Detection and Prevention. 28, 426-432 (13 pgs).
Gutheil, W., Reed, G., Ray, A., Anant, S., and Dhar, A. Crocetin: a agent derived from saffron for prevention and therapy for cancer. Current Pharmaceutical Biotechnology , 2012, 13, 173-179.
Siegel, R., Naishadham, D. and Jemal, A. Cancer Statistics 2013, CA Cancer J. Clin 63, 11-30, 2013.
Abdullaev FI, Frenkel GD. Effect of saffron on cell colony formation and cellular nucleic acid and protein synthesis. Biofactors 1992; .3:201-04.
Tarantilis PA, Morjani H, Polissiou M, et al. Inhibition of growth and induction of differentiation of promyelocytic leukemia (HL-60) by carotenoids from C. sativus L. Anticancer Res 1994;14:1913-18.
Giaccio, M. Crocetin from Saffron: An active component of an ancient spice. Clin. Rev. Food Sc. Nutr., 2004, 44, 155-172.
Sujata, V.; Ravishankar, G. A.; Venkataramn, L. V. Methods for the analysis of the saffron metabolites crocin, crocetins, picocrocin and safranal for the determination of the quality of the spice using thin layer chromatography, high performance liquid chromatography and gas chromatography. J. Chromatogr., 1992, 624, 497-502.
Li, N.; Lin, G.; Kwan, Y-W.; Min, Z-D. Simultaneous quantification of five major biologically active ingredients of saffron by highperformance liquid chromatography. J. Chromatogr., 1999, 849,349-355.

(Continued)

Primary Examiner — Yih-Horng Shiao
(74) Attorney, Agent, or Firm — Ballard Spahr LLP

(57) ABSTRACT

A fraction separated from crude crocetin by preparative HPLC, and identified using LC/MS and NMR as crocetinic acid, markedly regressed the proliferation and increased apoptosis in pancreatic cancer cells. Purified crocetinic acid showed more potency than 15 commercial or crude crocetin using proliferation and apoptosis as markers. Purified crocetinic acid also showed significant anti-tumorigenic activity against pancreatic cancer cells in a mouse model of pancreatic cancer. Given crocetinic acid's low toxicity, crocetinic acid could be used as a chemotherapeutic or chemopreventative agent for pancreatic cancer.

8 Claims, 8 Drawing Sheets

(56) References Cited

OTHER PUBLICATIONS

Abdullaev FI. Inhibitory effect of Crocetin on intracellular nucleic acid and protein synthesis in malignant cells. Toxicol Lett 1994; 70:243-51.

Nair SC, Kururumboor SK, Hasegawa JH Saffron chemoprevention in biology and medicine: a review. Cancer Biother 1995; 10:257-64.

Ashrafi M, Bathari SZ, Taghikhani M, et al.. The effect of carotenoids obtained from saffron from on histone H1 structure and H1-DNA interaction. Int J Biol Macromol 2005; 36:246-52.

Magesh, V.; Singh, J.P.; Selvendiran, K.; .Ekambaram, B.; Sakthisekaran, D. Antitumor activity of crocetin in accordance to tumor incidence, antioxidant status, drug metabolizing enzymes and histopathological studies. *Mol. Cell. Biochem.*, 2006, 287, 127-135.

Chryssanthi DG, Lamar FN, Iatrou G, et al.Inhibition of breast cancer cell proliferation by style constituents of different *Crocus* species. Anticancer Res 2007; 27, 357-62.

Dhar, A., Fogt, L., Subramaniam, D. and Anant, S. Cancer Stem Cells: Novel target using dietary components for prevention and treatment. Nutraceutical and Cancer ed Sarkar, F.S. p. 11-38, 2012 (Sep. 20, 2011) (31 pages).

Rosenberg L. Pancreatic Cancer: A review of Emerging Therapies. Drugs 59, 1071-1089, 2000.

Balasubramonian S, Chandraratna RA, Eckert, RL. A novel-retenoid related molecule inhibits pancreatic cell proliferation be a retinoid receptor independent mechanism via suppression of cell cycle regulatory protein function and induction of caspase-associated apoptosis. Oncogene 2005; 24:4257-70.

Mathews-Roth MM. Effect of crocetin on experimental skin tumors. Oncology 1982; 39, 362-64.

Lemoine NR, Hughes CM, Barton, C.M, et al. The epidermal growth factor receptor in human pancreatic cancer. J Pathol 1992; 166: 7-12.

Dhar A, Mehta S, Banerjee S, et al. Epidermal growth factor receptor, Is a novel therapeutic target for pancreatic cancer? Front Biosci 2005;10:1763-67 (7 pgs).

Yamanka Y, Freiss H, Korbin MS, et al. Coexpression of epidermal growth factor receptor and ligands in human pancreatic cancer associated with enhanced tumor aggressiveness. Anticancer Res 1993; 13:565-69.

Tsujimoto Y. Stress resistance conferred by high level of bcl-2 protein in human lyphoblastoid cell. Oncogene 1989; 4:1331-36.

Hawkins CJ, Vaux, D. Analysis of the role of bcl-2 in apoptosis. Immunol Rev 1994; 142: 127-39.

Oltvai ZN, Milliman CL, Korsmeyer SJ. Bcl-2 hetrodimerizes in vivo with a conserved homolog, Bax, that acclerates program cell death. Cell 1993; 74: 609-19.

Yin XM, Oltvai, ZN, Korsmeyer SJ. BH1 and Bh2 domains of Bcl-2 are required for inhibition of apoptosis and hetrodimerization with Bax. Nature 1994; 369: 321-23.

Lapidot, T, Sirard, Sirard, C, Vormoor, J et al (1994) A cell initiating human acute myeloid leukemia after transplantation into SCID mice. Nature 367; 645-648.

Bonnet D, Dick JE. (1997)Human acute myeloid leukemia is organized as a hierarchy that originates from a primitive hematopoietic cell. Nat Med 3, 730-737.

Gupta, S, Hussain, T, Mukhtar, H (2003)Molecular pathway for (−)-epigallocatechin-3-gallate-induced cell cycle arrest and apoptosis of human prostate carcinoma cells. Arch Biochem Biophys 410, 177-185.

Korkaya H, Paulson A, Charafe-Jauffret E, et al (2009). Regulation of mammary stem/progenitor cells by PTEN/Akt/beta-catenin signaling. PLoS Biol e1000121, vol. 7 (14 pgs).

Liu S, Dontu G, Wicha MS (2005) Mammary stem cells, self-renewal pathways, and carcinogenesis. Breast Cancer Res 7, 86-95.

Zhou BB, Zhang H, Damelin M et al (2009) Tumour-initiating cells: challenges and opportunities for anticancer drug discovery. Nat Rev Drug Discov. 8, 806-823.

Mwangi, SM, Srinivasan, S (2010) DCAMKL-1: A new horizon for pancreatic progenitor identification (Comment). Am J Physiol Gastrointest Liver Physiol 299, G301-G302.

May, R, Sureban, SM, Lightfoot, SA et al (2010) Identification of a novel putative/pancreatic stem cell marker DCAMKL-1 in normal mouse pancreas. Am J Physiol Gastrointest Liver Physiol 299, G303-G310.

Cohen Jr MM. (2003) The hedgehog signaling network. Am J Med Genet 123A, 5-28.

Office Action dated Oct. 8, 2014, in U.S. Appl. No. 14/246,305, filed Apr. 7, 2014.

Tanaka et al. Cancer Chemoprevention by Carotenoids. Molecules 17:3202-3242, 2012.

Wei et al. Expression of CD44, CD24 and ESA in pancreatic adenocarcinoma cells lines varies with local microenvironment Hepatobiliary Pancreat Dis Int 10:428-434, 2011.

Bao et al. Pancreatic Cancer Stem-like Cells Display Aggressive Behavior Mediated via Activation of FoxQ1. J Biol Chem 289:14520-14533, 2014.

Rosenberg L, Lipsett M.. Biotherapeutic approaches to pancreatic cancer. Expert Opin Biol Ther 2003; 3: 319-37 (Retracted in 2012).

Chai, X. et al. Metformin Increases Sensitivity of Pancreatic Cancer Cells to Gemcitanine by Reducing $CD_{133}+$ Cell Populations and Suppressing ERK/$P_{70}$S6K Signaling. Scientific Reports, 5:14404. www.nature.com/scientificreports. Published Sep. 22, 2015 (11 pages).

Rangarajan, P. et al. Crocetinic acid inhibits hedgehog signaling to inhibit pancreatic cancer stem cells. Oncotarget, vol. 6, No. 29, 27661-27673. Published Aug. 13, 2015.

Tang, F-Y et al. Lycopene inhibits growth of human colon cancer cells via suppression of the Akt signaling pathway, Mol. Nutr. Food Res. 2008, 52, 646-654.

Burris III, H.A. Improvements in Survival and Clinical Benefit With Gemcitabine as First-Line Therapy for Patients With Advanced Pancreas Cancer: A Randomized Trial. Journal of Clinical Oncology, vol. 15, No. 6 Jun. 1997: pp. 2403-2413.

Grunewald, R. et al. Saturation of 2',2'-difiourodeoxycytidine 5'-triphosphate accumulation by mononuclear cells during a phase I trial of gemcitabine. Cancer Chemotherapy and Pharmacology (1991) 27: 258-262.

Tempero, M.A. et al. Pancreatic Adenocarcinoma, Version 2.2012: Featured Updates to the NCCN Guidelines. J. Natl Compr Canc Netw. Jun. 1, 2012; 10(6): 703-713 (22 pages).

May, R. et al. Doublecortin and CaM Kinase-like-1 and Leucine-Rich-Repeat-Containing G-Protein-Coupled Receptor Mark Quiescent and Cycling Intestinal Stem Cells, Respectively. *Stem Cells*. 2009; 27(10) 2571-2579.

Samulitis et al. Gemcitabine resistant pancreatic cancer cell lines acquire an invasive phenotype with collateral hypersensitivity to histone deacetylase inhibitors. Cancer Biology & Therapy 16:1, 43-51, Jan. 2015.

Office Action (Final Rejection) dated Jun. 3, 2015, in U.S. Appl. No. 14/246,305, filed Apr. 7, 2014.

Office Action dated Feb. 17, 2016, in U.S. Appl. No. 14/246,305, filed Apr. 7, 2014.

Office Action (Final Rejection) dated Nov. 1, 2016, in U.S. Appl. No. 14/246,305, filed Apr. 7, 2014.

* cited by examiner

A. PROLIFERATION

B. APOPTOSIS

C. Flow Cytometry (Apoptosis)

D. Fluorescent Microscopy (Apoptotic Cells)

FIGURE 6

Prevention of Pancreatic Cancer using Novel Crocetin Compound Derived from Saffron Chetna Arora[1,2], Gregory Reed[3], William G. Gutheil[4] and Animesh Dhar[1,2]

Hematology and Oncology Division, Internal Medicine, KUMC[1], Kansas City VA Medical Center[2], Pharmacology, Toxicology and Therapeutics, KUMC[3] and Pharmaceutical Sciences, School of Pharmacy, UMKC[4]

ABSTRACT

Pancreatic cancer is the fourth leading cause of cancer deaths in the United States and no significant treatment is at present available. Although there are an increasing number of therapeutic options available for patients with advanced disease, their efficacy is time limited and non-curative. Presently approximately 50-60% of cancer patients in the United States utilize therapies derived from plants, herbs, flowers, or nutrients (complementary and alternative medicine [CAM]), exclusively or concurrently with their traditional therapies such as chemotherapy or radiation therapy. One such CAM therapy is "crocetin", a carotenoid compound isolated from the saffron plant. Recently it has been demonstrated by our laboratory that commercial crocetin treatment has potent antimitotic effects on both *in vitro* and *in vivo* pancreatic cancer xenograft models. We have recently purified novel crocetin compound from commercial or crude crocetin compound using HPLC and LC/MS. One of the fractions showed more potency than commercial or crude crocetin *in vitro* inhibiting proliferation and stimulating apoptosis

INTRODUCTION

Cancer is a major public health problem in the United States and many other parts of the world. Currently, one in four deaths in the United States is due to cancer (1). Pancreatic cancer is the 4th leading cause of cancer deaths in developing countries and worldwide and about more than 250, 000 cases are diagnosed annually (1, 2). There is a significant increase of cancer deaths due to pancreatic cancer (31,000 deaths in 2007 to approximately 45, 000 deaths in 2009) in the United States in recent days and there is no significant treatment available at present for pancreatic cancer (2). There are reports on use of saffron to treat various diseases, particularly cancer, by the ancient Indian, Egyptian, and Chinese cultures (3). Saffron, is present in the dry stigmas of the plant Crocus sativus L., and is used as a spice and a food colorant (4). Comprehensive chemical analysis of saffron extracts has demonstrated that major constituents include carotenoids, and in particular, crocetin (5). Recent study demonstrated that commercial or crude crocetin inhibited *in vitro* pancreatic cancer cell proliferation and tumor progression in a xenograft mouse model (6). Commercial or crude crocetin is combination of multiple components present as assessed by HPLC and LCMS. These compounds differ from crocetin in the number of sugars and methyl groups. Therefore, our approach will be to characterize subcomponents present in crude preparations of crocetin and to identify stable crocetin using preparative HPLC and LC/MS. All the fractions will be tested for proliferation and apoptosis as markers of antitumorigenic effect.

Figure 1. Crocetin Information

Crocus Flower Stigma of Crocus Flower Saffron

Structure of Crocetin

Crocetin is a carotenoid extract of the stigma of saffron flower (*Crocus sativus*) and it is an amphiphilic terpenoid. By structural analysis, it is an C-18 polyunsaturated carbon chain with COOH group at each end. It is used as anticancer drug in folklore Chinese Indian and Egyptian herbal medicine. It is reported to inhibit intracellular nucleic acid and protein synthesis (4). Experimental study on rat and human colon adenocarcinoma cells, pancreatic and breast cancer cells demonstrated promising effects on cancer. Crocetin inhibits pancreatic cancer cell proliferation and tumor progression in a xenograft mouse model (6).

HYPOTHESIS

The central hypothesis of this study is that crocetin inhibits cellular proliferation and stimulates apoptosis due to the impairment of growth related signaling pathways in pancreatic adenocarcinoma.

METHODS

HPLC, LC/MS and NMR : To fractionate crude crocetin by HPLC and LC/MS and to characterize the fractions using NMR.

Cell Culture: BxPC2 and Panc-1 cells were grown in DMEM medium and were plated onto 96 well microtiter plates for treatment with purified crocetin (PC) and or commercial or crude crocetin (CC) for 72 hours.

Proliferation Assay: Click-it Edu fluorescence assay using 96 well microtiter plates and Apoptosis Assay: Dead end Fluorometric Tunel Assay using 96 well microtiter plates and Vybrant apoptosis assay kit from Invitrogen containing Annexin V/Propidium iodide in 12 well culture plate using flow cytometric analysis were performed. Fluorescence microscopy was also performed using chamber slides.

Western Blot Analysis: Epigenetic (histone deacetylase [HDAC]) and its substrates [acetyl H3 lysine 14]), Proliferation (EGFR, phospho-EGFR, Akt, phospho-Akt) and Apoptosis (Bax and Bcl-2) markers were analyzed using Western Blot.

RESULTS

Figure 2
A. HPLC of commercial/crude crocetin
B. LC/MS of purified crocetin
C. $^1$H NMR of purified crocetinic acid (Fraction #5)

Figure 2. We performed 1D NMR in collaboration with William G. Gutheil of UMKC, to characterize Fraction #5 from HPLC, our initial findings using 1D NMR (1H) are presented here for characterization of crocetinic acid (Fraction #5).

A. HPLC of unfractionated commercial or crude crocetin using preparative Agilent 1500 series HPLC
B. B: LCMS chromatogram of preparative HPLC purified crocetinic acid (Fraction #5) using ABI 2000 QTrap with an electron spray ionization(ESI).
C. 400 MHz NMR spectrum of purified crocetinic acid showing the vinylic and methyl $^1$H resonances.

Figure 3: Proliferation and Apoptosis using different purified fractions.
PROLIFERATION
APOPTOSIS
Flow Cytometry (Apoptosis)
Fluorescent Microscopy Figure 3. Proliferation and apoptosis assay using click-it micro-plate proliferation assay and also using apoptosis kit after different concentrations (1, 10, 25 and 50μM) of treatment of Panc-1 cells. Apoptosis using flow cytometry and fluorescence microscopy was also presented using only one concentration (10μM) of treatment.

Figure 4: Comparison between Purified Crocetin (PC) and Crude Crocetin (CC) with Inhibition of Proliferation and Stimulation of Apoptosis in Pancreatic Cancer Cells

A. PROLIFERATION
B. APOPTOSIS

Figure 4. Panc-1 cells were incubated with purified crocetin (PC; Fraction #5) and crude crocetin (CC) at different concentrations (1, 10 25 and 50μM) for proliferation and apoptosis. Only 1 and 10μM of PC and CC were presented for proliferation, only 1μm was presented using fluorescence microscopy for apoptosis.

Figure 5. Effect of Purified Crocetin (PC) and Crude Crocetin (CC) on Histone acetylation, EGFR signaling and Bax/Bcl-2 on Pancreatic Cancer Cells.

Effect of Crude Crocetin (CC) and Purified Crocetin (PC) on Histone Acetylation (A),Proliferation (B) and Apoptosis (C)

POSSIBLE MECHANISMS OF CROCETIN

SUMMARY

One of the fractions (PC) derived from unfractionated crude crocetin (CC) using HPLC and LC/MS markedly regressed the proliferation and increased apoptosis in pancreatic cancer cells.

Purified crocetin (PC) significantly inhibits HDAC1 (histone deacetylase 1) and acetylated histone3 lysine 14, one of the substrates of HDAC1 following inhibition of EGFR and Akt phosphorylation than crude crocetin (CC).

Purified crocetin (PC; Fraction #5) showed more potency than crude crocetin (CC) in both proliferation and apoptosis.

CONCLUSION

Purified Crocetin showed significant anti-tumorgenic effect at lower doses in pancreatic cancer. Crocetin can be used as chemopreventive agent for pancreatic cancer in future.

FUTURE PLANS

To investigate effect of purified crocetin in xenograft mice pancreatic cancer animal model.

To explore the synergistic or additive or combinational effect of purified crocetin in combination with FDA approved known anticancer agents, paclitaxol, 5-FU, gemcitabine and cisplatin.

To undertake future phase 1 clinical trials using crocetin.

Figure 5. Panel A showed the inhibition HDAC and acetyl H3 Lys14 using Western Blot; Panel B showed EGFR activity both phosphorylated and total EGFR and also Akt phosphorylation that are significantly inhibited by 10μM PC; Panel C showed decrease of Bcl-2 and increase of Bax/Bcl-2 ratio that confirms apoptosis

REFERENCES
1. Jemal, A., Siegel, R., Ward, E., Hao, Y., Xu, J., and Thun, M. J. Cancer Statistics, 2009. CA Cancer J. Clin 59, 225-249, 2009.
2. Chua, Y. J. and Zalcberg, J. R. Pancreatic Cancer-is the wall crumbling? Annals of Oncology 19, 1224-1230, 2008.
3. Nair, S. C., Panikkar, B. and Panikkar, K. R. Antitumor activity of saffron (Crocus sativus). Cancer Lett. 1991;57:109-114.
4. Abdullaev, F. I. Cancer chemopreventive and tumoricidal properties of saffron (Crocus sativus L.) Exp. Biol. Med. 2002;227: 20-25.
5. Abdullaev, F. I. and Espinosa-Aguirre, J.J. Biomedical properties of Saffron and its potential use in cancer therapy and chemoprevention trials. (2004) Cancer Detection and Prevention, 28, 426-432.
6. Dhar, A., Mehta, S., Dhar, G., Dhar, K., Banerjee, S., Van Veldhuizen, P., Campbell, D. R. and Banerjee, S. K. (2009) Crocetin inhibits pancreatic cell proliferation and tumor progression in a xenograft mouse model. Mol. Cancer. Ther. 8, 316-323.

ACKNOWLEDGEMNTS: This work is supported by Kansas University Cancer Center Pilot Project Grant and VISN 15 Established Investigator Award. Special thanks to Dr. Shrikant Anant, Associate Director of KU Cancer Center, for his constant help in this project.

PURIFIED CROCETIN COMPOUND AND METHOD FOR TREATING, INHIBITING, AND/OR PROPHYLAXIS OF CANCER, SUCH AS PANCREATIC CANCER

CROSS-REFERENCE TO RELATED APPLICATIONS

This Application is a national stage filing under 35 U.S.C. § 371 of International Application No. PCT/US2011/001735, filed on Oct. 7, 2011, which claims the benefit of U.S. Provisional Application No. 61/344,879, filed Nov. 2, 2010, the contents of which are incorporated herein in their entireties.

STATEMENT REGARDING FEDERALLY SPONSORED RESEARCH OR DEVELOPMENT

The work leading to the present invention was supported by the U.S. Government, and specifically the U.S. Department of Veterans Affairs and the National Institute of Health. The U.S. Government therefore has certain rights in the invention.

FIELD AND BACKGROUND OF THE INVENTION

The present invention is generally directed to cancer prevention, treatment and therapy, and more particularly to a novel crocetin compound for use in pancreatic cancer.

Pancreatic cancer is one of the most lethal malignancies in humans and there is no effective conventional treatment available for treatment or cure of patients with pancreatic cancer. About 37,000 patients in US die of pancreatic cancer every year and it is a fourth leading cause of cancer deaths. Great demand of new effective drugs and alternative approaches has led to studies evaluating possible anti-cancer agents in fruits, vegetables, herbs and spices. Saffron, a spice and a food colorant present in the dry stigmas of the plant Crocus sativus L, was used to treat various diseases, particularly cancer by Greek and Chinese population in ancient times.

Crocetin, an important constituent of saffron, has been emerged as carotenoids by chemical analysis of saffron extracts which showed significant potential as an anti-tumor effect associated with saffron treatment in animal models and cell culture systems. Therefore, our laboratory has attracted to evaluate molecular mechanisms responsible for the anti-tumor effects of crocetin.

This project targeted towards pancreatic cancer seeks novel innovative approaches to develop new therapeutic strategies and will form a basis in future for developing a novel combinational therapy with high efficacy and low toxicity using crocetin in combination with known anticancer agents (Gemcitabine and 5-FU) generally used in pancreatic cancer. Collectively, these results will help to identify the comprehensive molecular targets for crocetin and contribute to our long-range goal of understanding the possible molecular mechanisms of treatment in patients with pancreatic cancer. Moreover, these studies will provide both evidence of effectiveness and scientific validation for using crocetin in pancreatic cancer and the foundation for the development of clinical trials incorporating this remedy.

ASPECTS OF THE INVENTION

The present disclosure is directed to various aspects of the present invention.

One aspect of the present invention includes purifying or fractionating crude crocetin to obtain a more potent agent than crude crocetin.

Another aspect of the present invention includes a novel crocetin compound.

Another aspect of the present invention includes a novel crocetin compound that is 50-times more potent than the crude crocetin.

Another aspect of the present invention includes a novel crocetin compound that has a low toxicity.

Another aspect of the present invention includes crocetinic acid.

Another aspect of the present invention includes the use of crocetinic acid as an anti-cancer agent.

Another aspect of the present invention includes the use of crocetinic acid in inhibiting proliferation of cancer cells.

Another aspect of the present invention includes the use of crocetinic acid in inhibiting proliferation of pancreatic cancer cells.

Another aspect of the present invention includes the use of crocetinic acid in stimulating apoptsis in cancer cells.

Another aspect of the present invention includes the use of crocetinic acid in stimulating apoptsis in pancreatic cancer cells.

Another aspect of the present invention includes the use of crocetinic acid in therapy, treatment, and/or prevention of cancer.

Another aspect of the present invention includes the use of crocetinic acid in therapy, treatment, and/or prevention of pancreatic cancer.

Another aspect of the present invention includes the use of crocetinic acid in therapy, treatment, and/or prevention of pancreatic cancer, in combination with other anticancer agent(s).

Another aspect of the present invention includes a composition including crocetinic acid.

Another aspect of the present invention includes a pharmaceutical formulation including crocetinic acid.

Another aspect of the present invention includes a diagnostic tool, marker, probe, assay, composition, and/or formulation including crocetinic acid.

BRIEF DESCRIPTION OF THE DRAWINGS

One of the above and other aspects, novel features and advantages of the present invention will become apparent from the following detailed description of the non-limiting preferred embodiment(s) of invention, illustrated in the accompanying drawings, wherein:

FIG. 6 is a Power Point illustration of preferred embodiments of the present invention.

DETAILED DESCRIPTION OF THE PREFERRED EMBODIMENT(S) OF THE INVENTION

The present invention is directed to developing a novel drug therapy using crocetin in pancreatic cancer which will improve survival rates. Therefore, oncology related medical companies, oncologist and pancreatic cancer patients will be interested. This study indicated for the first time that crocetin could be used as a novel therapy for pancreatic cancer due to significant anti-tumorogenic effect and thereby, can be of great therapeutic benefit in future.

Figure 1:
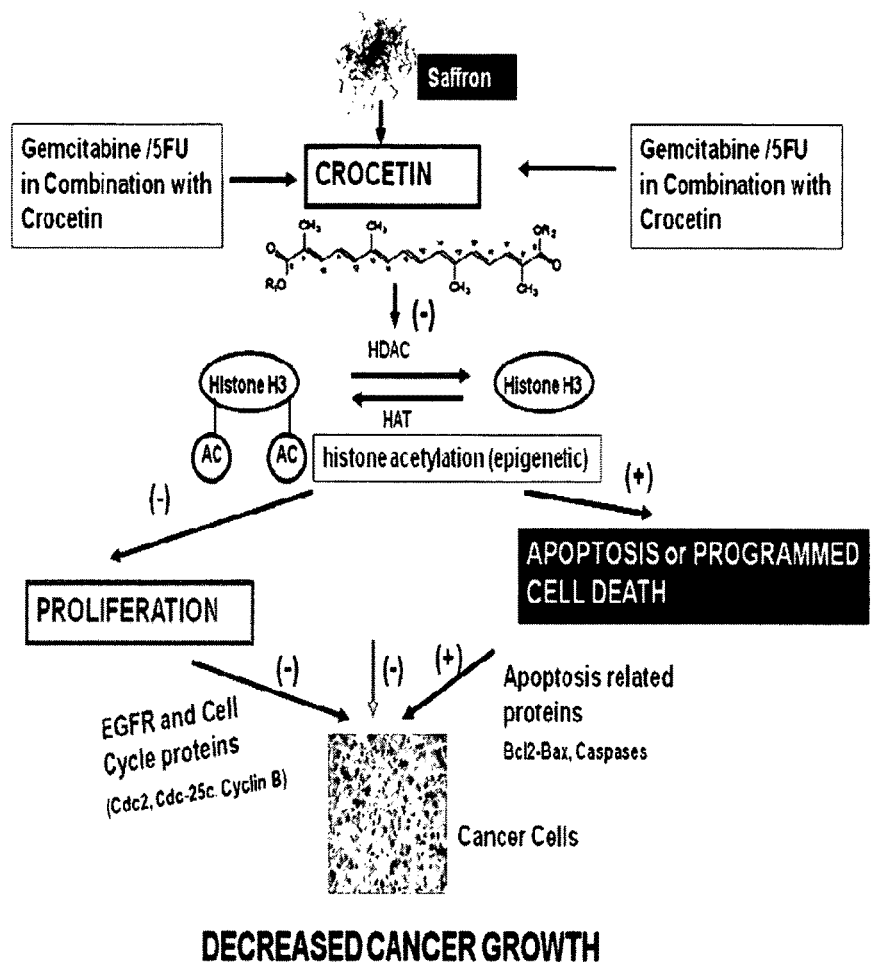
FIG. 1 is a schematic representation of possible mechanism action of novel crocetin compound on pancreatic cancer.

Crocetin, a carotenoid molecule isolated from saffron, has been demonstrated by our laboratory to have potent antimitotic effects both in in vitro and in vivo pancreatic cancer models. Thre possible mechanism of action of crocetin is described in FIG. 1.

Commercial or crude crocetin is a mixture of crocetinic acid and crocetin esters. We have recently fractionated crude crocetin using preparative HPLC, and LC/MS. One of the fractions derived from crude crocetin separated using HPLC and LC/MS markedly regressed the proliferation and increased apoptosis in pancreatic cancer cells. We have characterized the compound using 400 MHz NMR spectrum as crocetinic acid.

Our new data demonstrate that purified crocetin obtained in good yield from crude crocetin by alkaline treatment following HPLC and LC/MS is 50-times more potent in proliferation and apoptosis assays. We have generated new preliminary data using five fractions separated from crude crocetin. Peaks #1, #3 and #5 (crocetinic acid) show promising effect on inhibiting proliferation and stimulating apoptosis (FIGS. 2-5). The remaining two peaks showed little inhibition of proliferation using in vitro models. This project targeted towards pancreatic cancer seeks novel innovative approaches to develop new therapeutic strategies and will form a basis in future for developing a novel combinational therapy with high efficacy and low toxicity using crocetin in combination with known anticancer agents generally used in pancreatic cancer. Collectively, these results will help to identify the comprehensive molecular targets for crocetin and contribute to our long-range goal of understanding the possible molecular mechanisms of treatment in patients with pancreatic cancer. Moreover, these studies will provide both evidence of effectiveness and scientific validation for using crocetin in pancreatic cancer and the foundation for the development of clinical trials incorporating this remedy.

We have purified novel crocetin components from unfractionated commercially available crude crocetin that demonstrates more potency than crude crocetin. This study will develop novel potent crocetin component in the treatment of pancreatic cancer using in vitro and in vivo models and we will understand the molecular mechanisms of crocetin in relation to growth and apoptosis using novel purified crocetin alone or in combination with known chemotherapeutic drugs. This is the first time a systematic study on crocetin in pancreatic cancer will be undertaken. There is no effective treatment available to cure patients with pancreatic cancer; therefore, this study is essential for the development of complimentary, additive or combinational therapy using crocetin. Ultimately, this study will enhance our knowledge of the novel therapeutic interventions that could lead to clinical trials aimed at improving survival rates in pancreatic cancer.

Figure 2A:
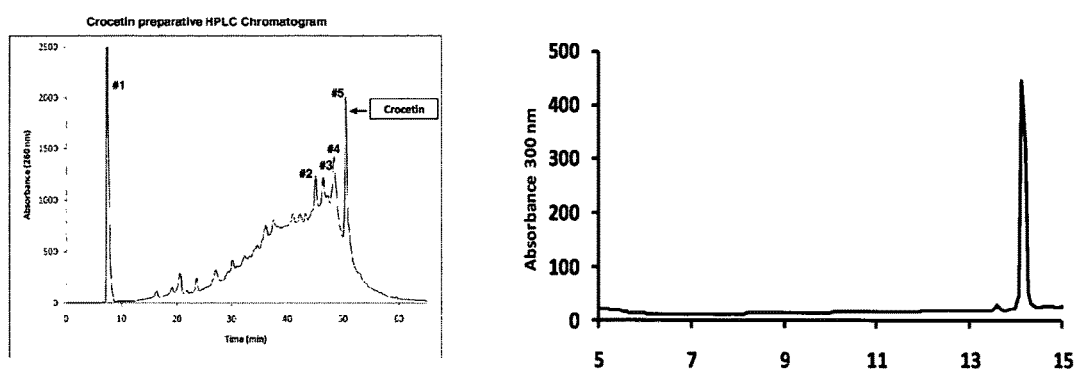
FIG. 2A illustrates LC/MS chromatogram of preparative HPLC purified crocetinic acid (Fraction #5)
Figure 2B:
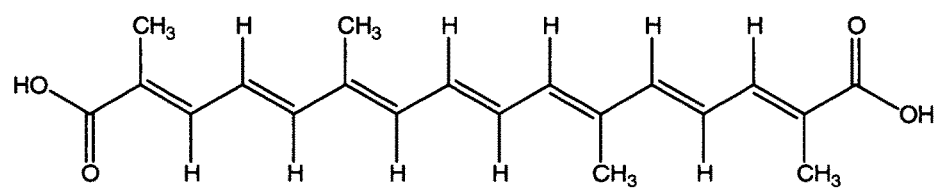
FIG. 2B illustrates structure of crocetinic acid.
Figure 2C:
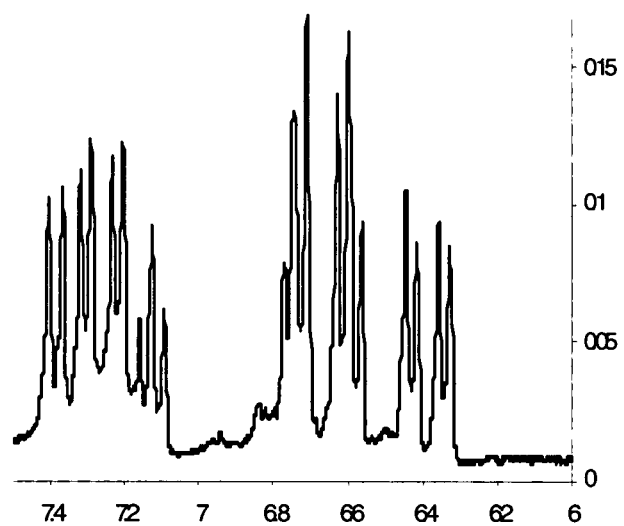
FIG. 2C illustrates 400 MHz NMR spectrum of purified crocetinic acid showing the vinylic and methyl $^1$H resonances.
Figure 2C:
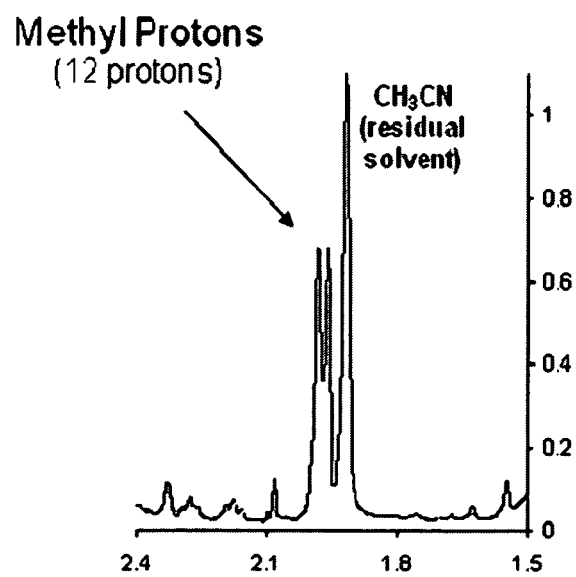
Figure 3:
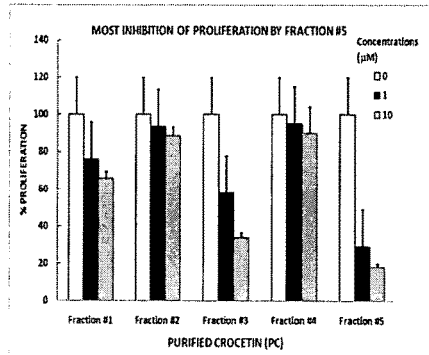
FIG. 3 illustrates proliferation and apoptosis using different purified fractions. Proliferation and apoptosis assay using click-it micro-plate (Invitrogen) proliferation assay and using Dead-end TUNEL apoptosis kit (Promega) using different concentrations (1 and 10 μM). Only 10 μM of 5 fractions was used for apoptosis using flow cytometry and fluorescence microscopy.
Figure 3:
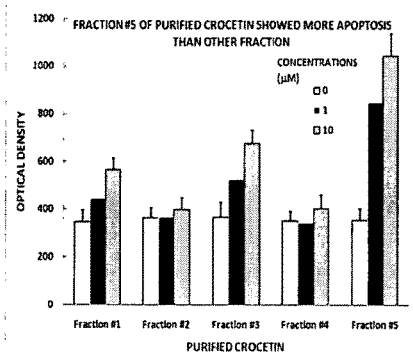
Figure 3:
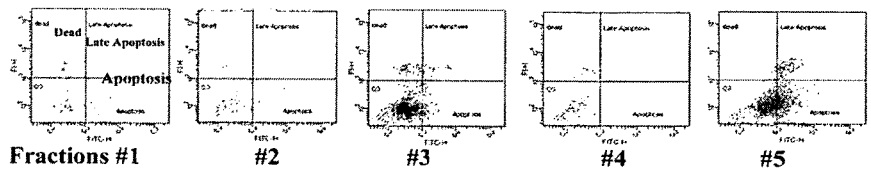
Figure 3:
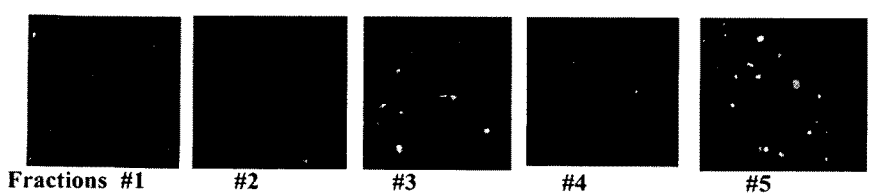
Figure 4:
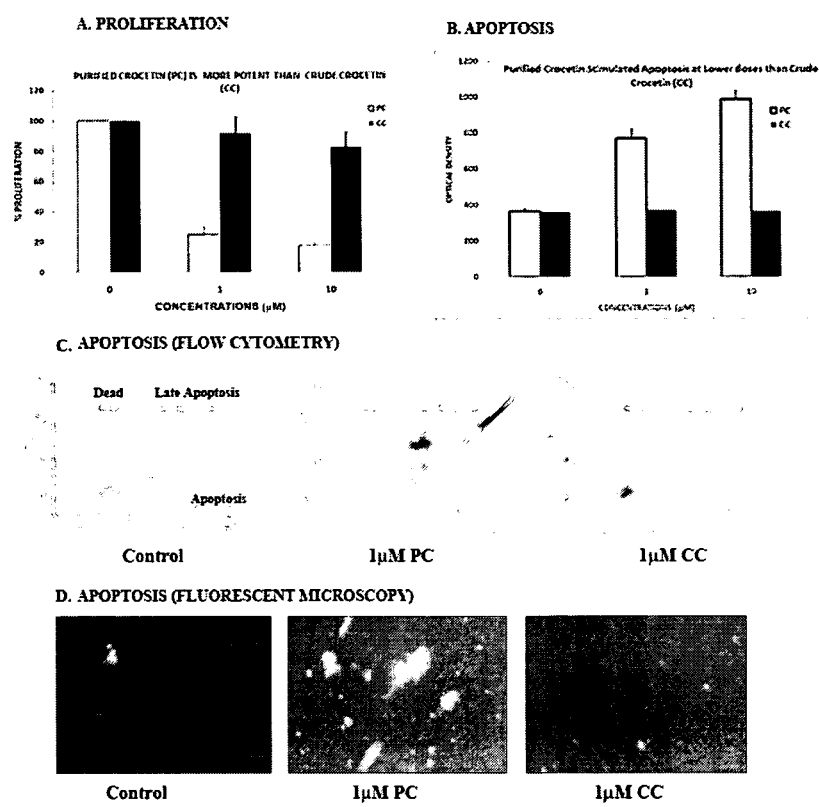
FIG. 4 illustrates comparison of inhibition of proliferation and apoptosis in Panc-1 cells. Panc-1 cells were incubated with PC (purified crocetin; Fraction #5) and CC (crude crocetin) at different concentrations (1, 10, 25 and 50 µM) for proliferation and apoptosis. Only 1 and 10 µM of PC and CC were presented for apoptosis using flow cytometry. Similarly, only 1 µm was presented using fluorescence microscopy for apoptosis.
Figure 5:
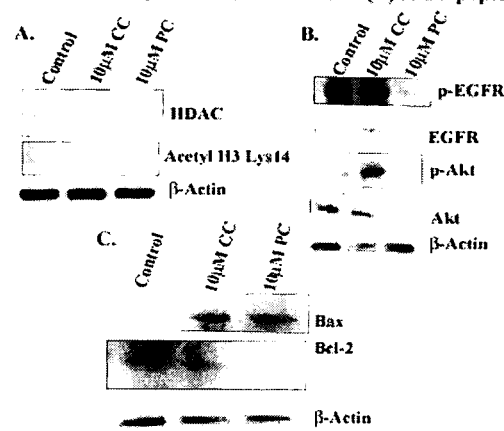
FIG. 5 illustrates effect of purified crocetin (PC) and crude crocetin (CC) on histone acetylation EGFR signaling and Bax/BcI-2 on Panc-1 cells. Panel A shows the inhibition HDAC and acetyl H3 Lys14 using Western Blot; Panel B shows EGFR activity both phosphorylated and total EGFR and also Akt phosphorylation that are significantly inhibited by 10 mM PC; Panel C shows decrase of BcI-2 and increase of Bax/BcI-2 ratio that confirms apoptosis. (PC=Purified Crocetin of Fraction #5 of FIG. 1A, CC=Crude Commercial Crocetin.)

Our preliminary data with purified crocetinic acid (Fraction #5 of HPLC; FIG. 2) showed greater antitumorigenic potency compared to crude commercial crocetin (FIGS. 3-5). The other 4 main constituents derived from HPLC of crude crocetin are glycoside and methyl esters of the crocetinic diacid. Some or all of these may also have anti-tumorigenic activity (FIG. 2). These various esters may be able to act as pro-drugs for active crocetinic acid, or may have increased potency. We propose to fractionate crude crocetin into all of its major components, to identify each component, and to characterize each for anti-tumorigenic activity. Our hypothesis is that several of the major constituents present in crude crocetin will have biological activity for inhibiting growth and stimulating apoptosis by modulating histone acetylation. The data is presented in FIGS. 1-5.

We performed 1D to characterize Fraction #5 as described in FIG. 3 (Research Strategy). Our initial findings using 1D NMR ($^1$H) are presented here for characterization of crocetinic acid (Fraction #5).

Proliferation and Apoptosis Assay with all 5 Purified Crocetin in Panc-1 Pancreatic Cancer Cells (FIG. 3)

We have generated new preliminary data using five fractions separated from crude crocetin (FIG. 2A) by HPLC. We treated Panc-1 cells with all 5 fractions and peaks #1, #3 and #5 (crocetinic acid) show promising effect on inhibiting proliferation and stimulating apoptosis (FIG. 5). Fraction #5 (crocetinic acid) showed most potent effect and the effect is 50 times greater than crude crocetin (FIG. 5). At least 50-100 µM crude crocetin were needed to achieve similar effect on those cells. The remaining two peaks showed little inhibition of proliferation using in vitro models.

Proliferation and Apoptosis Assay with Crude Crocetin and with Newly Purified Crocetin in Panc-1 and BxPC3 Pancreatic Cancer Cells (FIG. 4)

Our data demonstrates that purified crocetin obtained in good yield from crude crocetin by 0.01 mM sodium hydrooxide treatment following HPLC and LC/MS, and demonstrated about 50-times more potency in proliferation and apoptosis assays (FIGS. 4A panel and 3B). We treated Panc-1 pancreatic cancer cells with either purified crocetin or PC (Fraction #5 of FIG. 4A) derived from alkaline treatment or crude commercial crocetin or CC (1 and10 µM concentrations) for 48-72 hours. We have also used higher doses (25, 50 and 100 µM) in this experiment and it needs about 50-100 µM concentration of CC for inhibition of proliferation and increase of apoptosis at the level of 1 and 10 µm of PC. Treated cells were then labeled with Brdu and cells were assayed by Invitrogen Click-it Edu fluorimetric microplate proliferation kit and Promega Dead-end TUNEL apoptosis assay kit. Alkaline treatment (0.01M NaOH) of crude crocetin following HPLC showed more potency than crude crocetin in both apoptosis assay by Annexin5-FITC (Invirogen) Flow Cytometry and Fluorescence microscopy (FIG. 3; Panels C & D). Inhibition of poliferation using click-it microplate assay (Invitrogen) and stimulation of apoptosis is microplate assay (Promega) suggested 50 times more potent alkali treated purified PC (Fraction #5) than CC (FIG. 4).

Purified Crocetin (PC) Versus Crude Crocetin (CC) on Histone Acetylation, EGFR Signaling and Bax/Bcl2 on Pancreatic Cancer Cells (FIG. 5)

Panc-1 cells were treated for 72 hours by pure crocetin compound (PC) of fraction #5 (10 μm) isolated after alkaline treatment and HDAC and one of its substrate acetyl H3 (lysine 14) were monitored. There is significant inhibition of HDAC1 and its substrate acetyl histone H3 Lysine 14 that indicates histone modifications by inhibition of deacetylation (FIG. 5; Panel A) compared to crude crocetin (CC). EGFR phosphorylation is significantly inhibited by 10 μM PC than CC and both Akt expression and phosphoryalation also inhibited by PC (FIG. 4; Panel B). Apoptosis also showed significant increase in lower doses of PC using Bax/BcI-2 ratio (Panel C).This indicates that purified crocetin at lower doses significantly inhibited EGFR signaling pathways, in turn, affecting proliferation and also apoptosis by impairing Bax/Bcl2 ratio.

While this invention has been described as having preferred to sequences, ranges, steps, materials, structures, components, features, and/or designs, it is understood that it is capable of further modifications, uses, and/or adaptations of the invention following in general the principle of the invention, and including such departures from the present disclosure as those come within the known or customary practice in the art to which the invention pertains, and as may be applied to the central features herein before setforth, and fall within the scope of the invention and of the limits of the appended claims.

REFERENCES

The following references, and those cited in the disclosure herein, are hereby incorporated herein in their entirety by reference.

1. Dhar, A., Mehta, S., Dhar, G., Dhar, K., Banerjee, S., Van Veldhuizen, P., Campbell, D. R., and Banerjee, S. K. Crocetin inhibits pancreatic cancer cell proliferation and tumor progression in a xenograft mouse model. Mol. Cancer Ther. 2009; 8(2). February 2009, 315-323.
2. Jemal, A., Siegel, R., Ward, E., Hao, Y., Xu, J. and Thun, M. J. Cancer Statistics, 2009. CA Cancer J. Clin 59, 225-249, 2009.
3. Chua, Y. J. and Zalcberg, J. R. Pancreatic Cancer—is the wall crumbling? Annals of Oncology 19, 1224-1230, 2008.
4. Nair, S. C., Panikkar, B. and Panikkar, K. R. Antitumor activity of saffron (*Crocus sativus*). Cancer Lett. 1991:57: 109-114.
5. Abdullaev, F. I. Cancer chemo preventive and tumoricidal proporties of saffron (*Crocus sativus* L.) Exp. Biol. Med. 2002:227: 20-25.
6. Abdullaev, F. I. and Espinosa-Aguirre, J. J. Biomedical properties of Saffron and its potential use in cancer therapy and chemo prevention trials (2004) Cancer Detection and Prevention. 28, 426-43.
7. Gutheil, W., Reed, G., Ray, A. and Dhar, A. Crocetin: a agent derived from saffron for prevention and therapy for cancer. Current Pharmaceutical Biotechnology (accepted).

What is claimed is:

1. A method of treating or inhibiting cancer in a subject in need thereof, the method consisting of the step of administering to the subject:
    (a) an effective amount of a purified crocetinic acid compound;
    (b) gemcitabine; and
    (c) 5-fluorouracil (5-FU).
2. The method of claim 1, wherein the cancer comprises pancreatic cancer.
3. The method of claim 1, wherein the crocetin compound is administered orally or intravenously.
4. The method of claim 1, wherein the subject is a human or an animal.
5. The method of claim 1, wherein the effective amount is less than the amount of crude crocetin needed to achieve the same effect, wherein the crude crocetin is a mixture of crocetinic acid and crocetin esters.
6. The method of claim 5, wherein the effective amount is at least 50 times less than the amount of crude crocetin needed to achieve the same effect, wherein the crude crocetin is a mixture of crocetinic acid and crocetin esters.
7. The method of claim 5, wherein the purified crocetinic acid compound has a high-performance liquid chromatography (HPLC) spectra as shown in FIG. 2A (left panel).
8. The method of claim 1, further comprising alkaline treatment of a crude crocetin compound to obtain the purified crocetinic acid compound, wherein the crude crocetin compound is a mixture of crocetinic acid and crocetin esters.

* * * * *